United States Patent [19]

Goldberg et al.

[11] Patent Number: 4,801,463

[45] Date of Patent: * Jan. 31, 1989

[54] CONTINUOUS CHEESE-MAKING PROCESS UTILIZING AN IMMOBILIZED RENNET ENZYME REACTOR

[75] Inventors: Bruce S. Goldberg, Clifton; Richard Y. Chen, Livingston, both of N.J.

[73] Assignee: FMC Corporation, Philadelphia, Pa.

[*] Notice: The portion of the term of this patent subsequent to Aug. 25, 2004 has been disclaimed.

[21] Appl. No.: 24,842

[22] Filed: Mar. 18, 1987

Related U.S. Application Data

[63] Continuation of Ser. No. 641,445, Aug. 16, 1984, abandoned.

[51] Int. Cl.$^4$ .................. A23C 19/024; A23C 19/04; C12M 11/08; C12M 1/40
[52] U.S. Cl. ........................................ 426/36; 426/40; 435/180; 435/182; 435/288; 99/452
[58] Field of Search ............... 426/36, 40; 435/180, 435/182, 219, 288; 99/452

[56] References Cited

U.S. PATENT DOCUMENTS

| | | | |
|---|---|---|---|
| 3,809,613 | 5/1974 | Vieth et al. | 435/288 |
| 3,945,310 | 3/1976 | Stenne | 435/36 X |
| 4,169,014 | 9/1979 | Goldberg | 435/182 |
| 4,292,409 | 9/1981 | Cremonesi | 435/288 |
| 4,689,302 | 8/1987 | Goldberg et al. | 435/288 |

FOREIGN PATENT DOCUMENTS 5856670  9/1981  Japan ................... 435/288

OTHER PUBLICATIONS

Olson, et al., Immobilized Enzymes on Food and Microbial Processes, Plenum Press, N.Y., 1974, pp. 22–35, 162, 163 & 176–179.

Pitcher, Jr., W. H., Immobilized Enzymes for Food Processing, CRC Press, Inc., Boca Raton, Florida, 1980, pp. 176–179.

Primary Examiner—David M. Naff

[57] ABSTRACT

Cheese is made continuously by flowing milk through a spiral flow path of a reactor containing an immobilized enzyme such as rennet which coagulates the milk. The spiral flow path is formed by a spirally wound microporous sheet containing the immobilized enzyme. Adjacent surfaces of the sheet are spaced apart with a spacer which can be a plurality of microporous ribs or a sheet in open net form.

20 Claims, 5 Drawing Sheets

CONTINUOUS CHEESE-MAKING PROCESS UTILIZING AN IMMOBILIZED RENNET ENZYME REACTOR

This application is a continuation of application Ser. No. 06/641,445, filed Aug. 16, 1984, now abandoned.

This invention relates to an improved method for forming cheese in a continuous manner. More particularly, this invention relates to a continuous process for making cheese starting at low and up to high temperatures, e.g. up to 40° C., or a combination of the two in steps to cause clotting and cheese curd formation. Still further, this invention relates to a method whereby repeat treatment of partially or fully reacted milk is utilized in a cheese-making process including reutilization of any residual unreacted values which may further be exhausted of any valuable constituents thereof.

BACKGROUND OF THE INVENTION

In a typical cheese-making operation, milk is inoculated with an appropriate culture often called a starting culture or bacterial starter. The bacterial starter causes acidity to develop in the cheese as a result of lactic acid formation. The various bacterial additions also produce various cheese types. Thereafter the thus inoculated milk is contacted by stirring with an appropriate amount of enzyme rennet used to coagulate the casein in the milk to produce the cheese curds. While coagulation takes place, the vessel contents are not stirred. This batch reaction may be conducted in another tank although the same tank may be utilized. Thereafter stirring is resumed; curd formation takes place, and whey is separated from the curds. Thereafter a salt wash may be used to separate further the whey from the cheese. Whey, of course, is not affected by rennet.

Typically the feedstock is at a proper pH, e.g. about 6-6.5, and temperature and thus produces the controlled quality of cheese sought to be obtained. The present invention, however, does not relate to acid precipitation such as at a pH of 4 to 5, e.g. for cottage cheese.

As it is evident from the above description, cheese-making is essentially a batch process wherein different vessels may also be used to produce different reactions. These operations are described in literature such as Van Slyke and Price, "Cheese", Orange Judd Pub. Co., New York, NY (1949).

In an endeavor to reduce the large scale batch vessels or to speed up the production of cheese, a number of batch or semi-batch operations have been proposed.

One of the proposed methods requires an enzyme deposited on flat surfaces. The substrate, that is the bacterially inoculated material, is flowed past the enzyme. Thus the substrate is being treated in a continuous manner.

These surface deposited enzymes, of course, have imposed a great limitation on the flow rates, especially since the enzyme deposition has been by adsorption on a surface when these enzymes have been sought to be deposited on the surface.

Additionally, long pipe reactors have been proposed such as where rennet and milk are mixed in the pipe reactor, and then dumped in a vessel, or a long pipe reactor for a flow method in which the reaction would take place on the walls of the pipe containing the adsorbed enzymes.

According to the last method the bacterially inoculated material flows through the pipes at low velocities so as not to strip, by turbulent flow, the enzymes deposited on the wall surfaces. As it is well known, at low velocities the laminar flow conditions obtain and the velocity profile in a pipe reactor often resembles substantially a parabola. As the reaction rates are different based on the velocity profile as well as the turbulence or lack thereof, the production quality or yield often suffered.

Additionally, various enzymes deposited on filter surfaces likewise have been sought to be immobilized by other enzyme carriers which were retained on the filter material, e.g. due to mesh constraints or filter material type for filter leaves of the apparatus. The fluid flow had been sought to be such as to cause the reaction to be continuously conducted.

However, one of the great shortcomings of the prior art batch, wall, or leaf filter type of reactors has been the inexact rennet to milk ratio caused by improper mixing, or clogging and/or stripping of these surface-deposited materials which all have affected the fairly sensitive rennet to milk ratios, thus adversely affecting the necessary quality, control and yields.

Moreover, only a substrate of a high degree of purity could be employed to produce the desired or sought-after enzymatic conversion at sacrifices in reaction rates and flow rates. As a general proposition, all substrate materials which carried particulates such as proteins, fats, coagulants, etc., would cause to blind, i.e. clog, the reaction surfaces. Moreover, these particulates will also cause to strip the enzyme from the reaction surfaces. Hence, substantially non-uniform, noncontrollable reactions would occur. As a result, only partially reacted products could be obtained which then thereafter had to be further treated or mixed to be normalized as to content, quality, etc., to obtain the sought-after product.

In order to remove the disadvantages of enzyme stripping and low flow rates, various other approaches have been used such as pulsating reactors which supposedly attempt to overcome the disadvantages of the prior art apparatus limitations, yet rely on the batch process advantages of quiescent coagulation followed by pulsation.

Other attempts have been made to fluidize a reaction using fluid bed principles. For example, the enzyme is deposited on the fluidized heterogeneous phase with a substrate forming the liquid phase being reacted upon by the fluidized particles. As it is known from fluid bed mechanics, considerable abrasion exists between the fluidized particles which results in the loss of enzyme. Thus fixed and fluid bed reactors have been suggested with various attempts made to improve the mass transfer, the rates and/or interface restrictions in the prior art reactors or processes.

Needless to say, these complications have introduced numerous problems such that the continuous cheese-making process has been a long sought-after goal. Hence the present process has as an objective the production of cheese at substantially improved rates, with high quality, in a consistent and controlled manner at either low or high temperatures, with a tolerance for a high percentage of particulates in the substrate, excellent rennet to milk ratios, repeatable, controlled precise exposure to rennet, with substantial elimination of operator error, and also if desired a cheese without rennet being present.

THE PRIOR ART

In evaluating the present invention, the applicant is aware of the following art:

U.S. Pat. No. 3,796,175 granted Oct. 30, 1973 to Berdelle-Hilge;
U.S. Pat. No. 3,884,641 granted May 20, 1975 to Kraffczyk et al.;
U.S. Pat. No. 3,945,310 granted Mar. 23, 1976 to Stenne;
U.S. Pat. No. 4,016,293 granted Apr. 5, 1977 to Coughlin et al.;
U.S. Pat. No. 4,048,018 granted Sept. 13, 1977 to Coughlin et al.;
U.S. Pat. No. 4,102,746 granted Jul. 25, 1978 to Goldberg;
U.S. Pat. No. 4,169,014 granted Sept. 25, 1979 to Goldberg;
U.S. Pat. No. 4,292,409 granted Sept. 29, 1981 to Cremonesi;
U.S. Pat. No. 4,416,993 granted Nov. 22, 1983 to McKeown.

BRIEF DESCRIPTION OF THE PRESENT INVENTION

In accordance with the present invention, it has now been found that rate quality, flow, and mixing constraints imposed by an enzyme deposited on a flat surface or suspended particle may be substantially avoided by employing a microporous sheet upon and in which the enzyme is immobilized. Thus rennet is not in the final product. At the same time, microporosity is maintained in the sheet while the advantages of a flow-by reactor are maintained and, more importantly, the high particulate fluids may also be treated at great advantage. The reactor design and the advantages thereof have been disclosed in a companion application Ser. No. 595,954 filed Apr. 2, 1984, now U.S. Pat. No. 4,689,302.

However, the benefits of the present process accrue as a result of the highly controllable flow characteristics, the precise milk to rennet ratios, the enzyme orientation or disposition, the enzyme immobilization, the quality control, the porosity considerations, and the flow distribution which is obtained by the process steps herein. Other advantages are, for example, yields which are highly controllable; quality which is repeatable; the freedom to make changes including saving milk (as rennet is not present until contacted with the immobilized enzyme); the starter culture may be easily metered in a continuous manner; rennetting can be done independent of coagulation; rennetting at low temperature can be followed by coagulation elsewhere; off line coagulation may be done later; rennetting and coagulation may be done in a continuous tube; rennetting could also be done at almost coagulation temperature; the pipe reactor can be shut down and reactivated without microbial contamination (following proper precautions), etc.

These advantages are obtained without the prior art disadvantages such as clogging or blinding of the reactor surfaces. Still further, the great benefit vis-a-vis for example the filter type reactors, has been realized by the ability to process particulate containing substrates which contrariwise to the prior art shortcomings, do not substantially strip, abrade, or remove the immobilized enzymes. Rather, the present process, as practiced, improves the flow characteristics, the fluid distribution, and at the same time does not allow the particulates to grow to such size as to cause macro-curd formation.

In accordance with the present invention, it has also been found that the fluid distribution aids immeasurably to the production of a high quality product by the immobilized rennet, as precise milk to rennet ratios may be computed, including obtaining precise time, temperature, and space velocity conditions.

While the exact mechanisms responsible for the reaction are not known, it is believed that the fluid flow properties interact with the microporous, reticulated three-dimensional matrix in which the immobilized rennet is held. It is postulated, without being bound by this theory, that the individual liquid "cell" residence time in the reactor is beneficially improved by the microporosity, yet all the flow reactor, but more precisely, flow-by reactor process characteristics are retained.

It is believed that the flow characteristics are especially beneficial because the partially reacted or even reacted and not yet fully coagulated fluid does not clog the surfaces, but rather strips these without stripping the rennet. As a further benefit, a flow reactor configuration, as further explained herein and which forms one of the process embodiments, has been improved by the rib structure being also of a microporous nature and carrying the immobilized enzyme rennet. A mesh material likewise may be of a microporous nature carrying the immobilized enzyme rennet and disposed in a reaction zone. Use of the mesh device forms another embodiment herein. These flow division or distribution means further aid and yet not impede the reaction causing thus the enzyme initiated reaction to continue in an advantageous manner with controlled turbulence further benefiting the process.

Turning now to the specific method whereby the immobilized rennet is obtained, in previous U.S. Patents such as No. 4,102,746 and No. 4,169,014, the method of immobilization has been disclosed. These patents are incorporated by reference herein and need not be discussed in greater detail. However, the immobilization technique employed in these patents is useful for the employment of the present enzymes so that the immobilization in the three-dimensionally reticulated microporous structure can be obtained in a similar manner with excellent results.

Based on the above disclosure and based on the studies as conducted, it is apparent that it is not merely the enzyme-reactor surface causative effect that plays a role, but also that the three-dimensional structure contributes to the overall reaction in the fluid flow-by, acting through the in-depth deposited enzyme. In other words, there is a benefit which is far greater than attributable to the surface catalyzed reactions. The results go beyond the expected results which are merely obtained from the surface catalyzed reactions and are gained by employing in the reaction three-dimensionally immobilized rennet which somehow has an ability to influence the reaction conditions in the flow-by reactor, yet without any substantial drawbacks of the surface deposited enzymes, e.g. stripping, abrading, clogging, etc.

Based on these considerations and based on the various alternatives which are possible to employ, the further benefits accrue as a result of the following advantages. One, there is an improved ability to exhaust the substrate constituents which may be usefully converted by the enzyme. The typical discharge of useful components in whey, e.g. when making cheddar cheese, in accordance with the prior art, is about 89.4% of whey, of which water is 83.1%, of which the residue, 6.3% on dry weight basis, are useful. In accordance with the present process, by being able to react the particulate-containing substrate from which coagulated curd material has been substantially removed, the results have been improved such that substantially entirely the components convertible to cheese by the action of rennet may be converted. Of the still useful material left in the whey, this may, of course, be treated in a different manner to convert it to different products, including cheeses made from whey, e.g. Ricotta cheese.

As another benefit, the rate of coagulation of casein can be carefully controlled by raising the temperature. This characteristic may be used in conjunction with or made dependent upon the flow rate. Thus the coagulation condition and the subsequent coagulation may be appropriately controlled without affecting the rennet, the quality or consistency of the cheese, etc. The temperature effect upon rennet under these conditions is considerably better monitored and the enzyme is considerably less susceptible to damage, because the conditions are essentially adiabatic due to the temperature maintenance being capable of very careful control. Also staged reactors with different flow and/or temperature conditions may be used.

One of the principal factors which has been found to affect the product and process has been the spacing of the sheets. For example, the range from 0.050 to 0.003 inches has been found to be useful with 0.040 to 0.005 being the preferred range for the critical spacing distance. At the lower end of the spacing range, the pressure drop becomes too great; at the higher end the renneting reaction is less susceptible to precise control.

BRIEF DESCRIPTION OF THE DRAWINGS

In the drawings in which similar elements are given similar reference characters and wherein various aspects and embodiments of the invention are illustrated.

DESCRIPTION OF THE PREFERRED EMBODIMENTS

A type of microporous sheet 30 is shown and described in U.S. Letters Pat. No. 4,102,746 issued July 25, 1978 in the name of Bruce S. Goldberg and assigned to the assignee of the instant invention. In addition, other microporous plastic and rubber sheets can be used, e.g. as shown in U.S. Pat. No. 4,226,926, also assigned to the assignee of the instant invention.

Proteinaceous preparations, for example enzymes, can be immobilized upon the silica fragments on the surface of the sheeting and in the pores of the sheeting employing the techniques described in U.S. Pat. No. 4,102,746 and using with material such as described in U.S. Pat. No. 4,226,926. Other suitable techniques are also known in the prior art.

Because of the pore 32 size being in the range of 0.01 microns to 100 microns, the presence of fat globules, protein, cheese solids and any materials which can coagulate to form globules can quickly seal the pores, and reduce or completely cut off any flow through the reactor. Since fat globules are larger than the pore size, either alone or with a number combined, these globules soon coat the surface penetration and prevent any of the feedstock from entering into the pores. These fat globules must be removed by filtration of the feedstock before it is introduced into the reactor system or periodically the feedstock stream must be stopped and the reactor system backwashed by the use of suitable material, such as water, and causing it to flow reversibly through the reactor system, that is from surface to surface.

Figure 1:
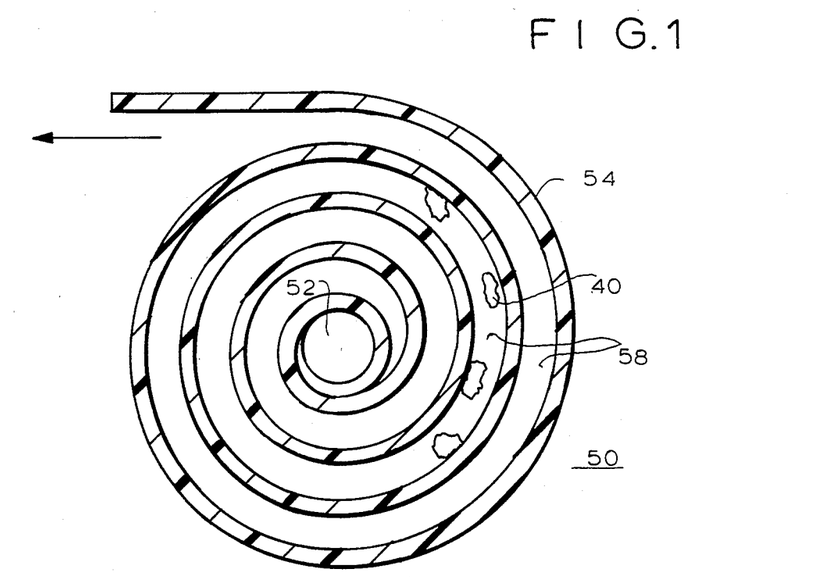
FIG. 1 is a side elevation, in section, of a jellyroll spiral configuration reactor constructed in accordance with the concepts of the invention and with the spacing layer omitted for the sake of clarity.
Figure 1A:
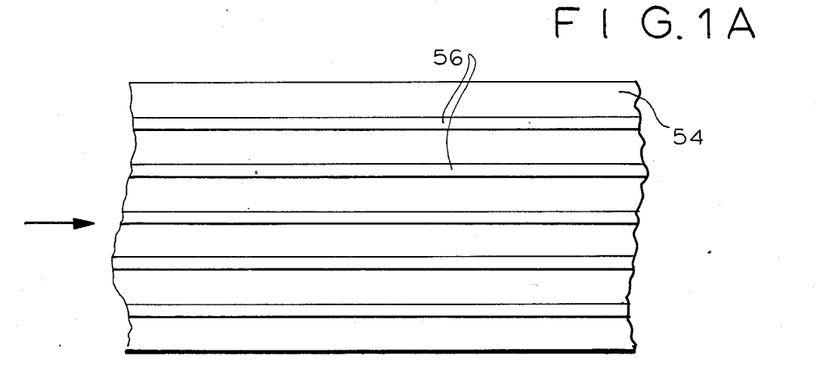
FIG. 1a is a fragmentary bottom plan view of a material from which the spiral reactor of FIG. 1 is formed and showing the ribs formed on one surface thereof.
Figure 2:
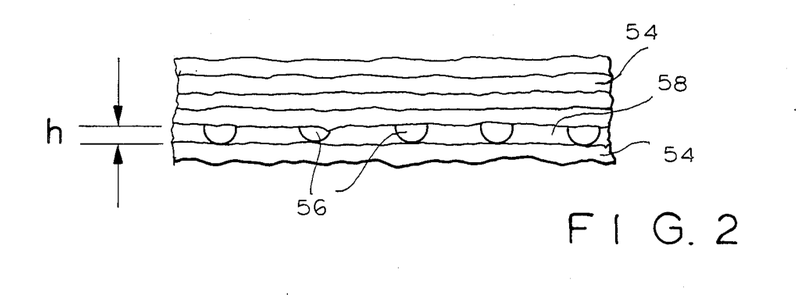
FIG. 2 is a front elevational view of a portion of the spiral reactor of FIG. 1 and showing the manner in which the ribs on one surface of the material keep adjacent convolutions of the reactor separated.

Turning now to FIG. 1, there is shown a spiral reactor 50 constructed to achieve the results of the present process. The reactor 50 comprises a porous core 52 of appropriate diameter and volume such that it can accept the feedstock introduced into the reactor 50 or to receive the converted feedstock to conduct it from the reactor 50. The spiral reactor 50 is substantially made up of microporous sheets 54 having a proteinaceous preparation immobilized on or in the pores of the sheets 54. However, the sheets 54 are modified to include a plurality of longitudinal ribs 56 on one surface thereon as is shown in FIGS. 1a and 2. The ribs 56 contact the adjacent convolutions of the spiral to keep them separated and to establish a series of passages 58 therebetween in conjunction with the spiral convolutions themselves. The height h (see FIG. 2) is so chosen that a desired flow-through reactor 50 is attained while insuring proper conversion of the feedstock. The height h of the ribs 56 has been found to be in the range of 0.003" to 0.050" and most particularly about 0.005" to 0.040". The height will, of course, have to be altered depending upon the feedstock employed. The total space available for feedstock flow is identified as the void volume and measured in cubic centimeters.

Figure 3:
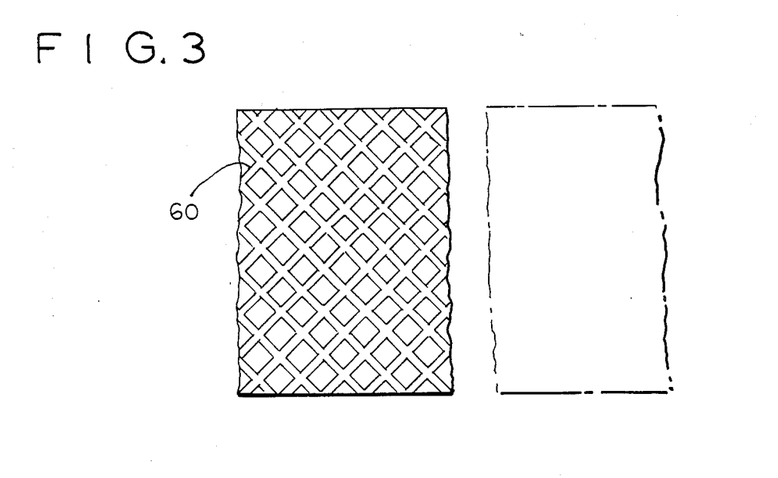
FIG. 3 is a fragmentary top plan view of a net-like spacing sheet which can be used with the support medium to construct a reactor in accordance with the concepts of the invention.
Figure 3A:
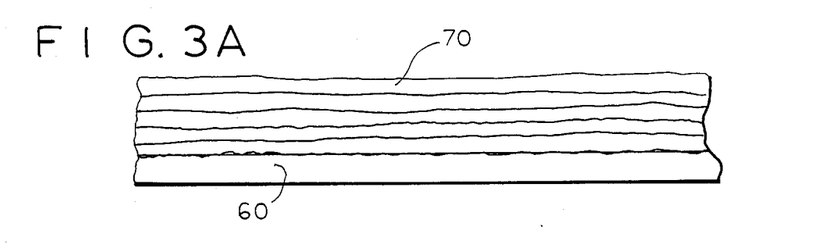
FIG. 3a is a fragmentary side elevation of the spacing sheet of FIG. 3 positioned adjacent one surface of the support medium.

Alternatively, a spacing sheet 60 as shown in FIGS. 3 and 3a may be employed instead of the raised ribs 56. The spacing sheet 60 is made of a flexible plastic or rubber material and in an open fish net format to assure light weight and flexibility. The spacing sheet may be made of a microporous material with an enzyme immobilized thereon. Spacing sheet 60 is simply laid atop a microporous sheet 70 as shown in FIG. 3a. Even though the surfaces of the spacing sheet 60 are substantially flat, the surface of the sheeting will rest on a number of peaks on the surface of sheet 70, providing, along with the open net format of the sheet 60, sufficient passages to permit the feedstock to pass the spacing sheet 60.

Figure 4:
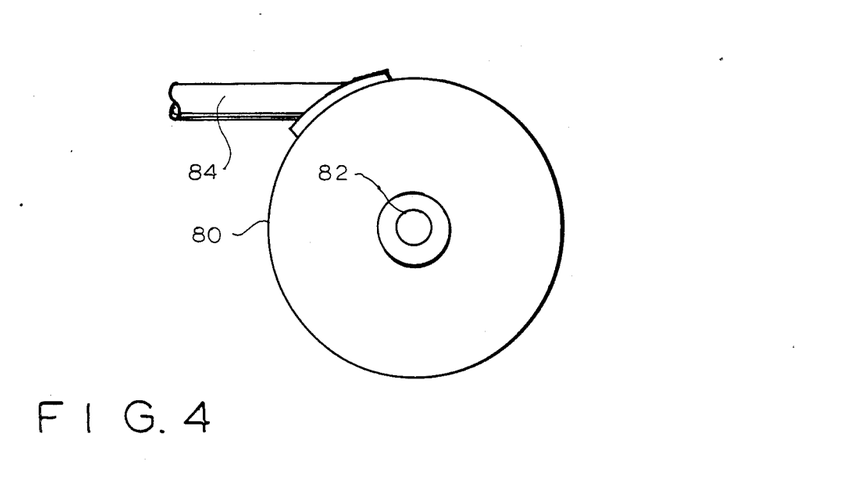
FIG. 4 is a simplified side elevational view of the completed reactor with inlet and outlet pipes connected thereto.

The reactor 50 is completed as shown in FIG. 4 by encapsulating the entire unit in a suitable housing 80. A pipe 82 is provided to gain access to the core 52 and plenum 84 is to provide access to the free end of the reactor. Although it is preferable to introduce the feedstock under suitable pressure into the core 52 of the reactor 50 and remove the converted feedstock from the free end of the reactor 50, the opposite flow pattern can also be used, namely introduce the feedstock to the free end and remove the converted feedstock from the core 52.

The microporous sheeting together with a spacing layer, whether ribs 56 or spacing sheet 60, are wound upon core 52 to form the spiral configuration shown in FIG. 1. As the feedstock flows along the passage 58, it is sufficiently exposed to enzyme to convert the feedstock to a high degree.

The spiral reactor 50 may be formed of a stack of individual microporous sheets 54, which are about 0.020 inches thick. It may also be formed by winding on itself a 90 inch length of 0.020 inch thick microporous material to produce a layer 1 inch thick and having a width of 3 inches. Considering that both sides of the sheets 54 are available, a total surface area of 270 square inches, reduced by the areas of contact of the sheet 54 edges with the housing 80, about 240 square inches of surface is effective. Employing ribs 56 having a height h of 0.010 inches and winding the sheets 54 on a porous core 52, 1 inch in diameter and 3 inches long, results in a reactor 50 having an outside diameter of 2 inches and a void volume or flow path volume of between 30 and 40 cubic centimeters. When potted, that is with the housing 80 in place, the outside diameter is 2¾ inches thick.

With the enzyme lactase immobilized on the sheets 54, as set out in U.S. Pat. No. 4,169,014 identified above, and employing skim milk adjusted to a pH of 5.1 at a flow rate of 10 milliliters per minute at 40° C. with a residence time of 3 to 4 minutes, reactor 50 is capable of hydrolyzing 90% of the lactose in the skim milk.

If a reactor 50 is constructed using a spacing sheet 60 of a fish net format having open areas from 50-90% but preferred in the range of 70-80% of the area of a continuous sheet of the same dimensions and a thickness of 0.010 inches, the available void volume will be about 50 cubic centimeters. Using the same feedstock under the same conditions set out in the previous example, approximately the same percentage of lactose in the skim milk will be hydrolyzed. It has been found that in actual practice conversions of the feedstock have reached values as high as 90%. The flow path through the reactor 50 is assumed generally to be laminar, but in practice it has been found to have a random flow, the flow causes eddies, and in some cases may also pass through the sheet itself.

Various coagulation or clotting time studies at various temperatures and residence times have been illustrated in the drawings. These will be described in greater detail in the examples herein. In brief, the flow rate of the feed at the given temperature is indicated from which the contact or residence time is calculated based on the reactor volume. Thereafter the actual clotting or coagulation time is correlated again at the particular temperature used. These data will be described and explained below in the Examples as these relate to FIGS. 5, 6 and 7.

These and others benefits will be further pointed out herein below with reference to the specific embodiments wherein the examples illustrate merely the various aspects of the invention and are not intended to limit the broader scope of the invention.

EXAMPLE 1

A calf-rennet milk clotting enzyme was immobilized on a spiral reactor as shown in FIG. 1 for testing on continuous coagulation of skim milk. The milk-clotting apparatus was set up for the coagulation time study and the parameters of temperature and residence time were studied.

The calf-rennet clotting enzyme was immobilized on the spiral reactor by using the standard immobilization technique described in U.S. Patents such as No. 4,102,746 and No. 4,169,014.

Using the milk-clotting enzyme immobilized spiral reactor, continuous coagulation on skim milk was achieved. Skim milk was pumped through the rennet immobilized reactor at various flow rates (residence times) and was coagulated at 30° C. The obtained data were depicted in FIGS. 5 and 6.

Residence time (flow rate), temperature and pH of skim milk were the major factors that affect the coagulation time.

Figure 6:
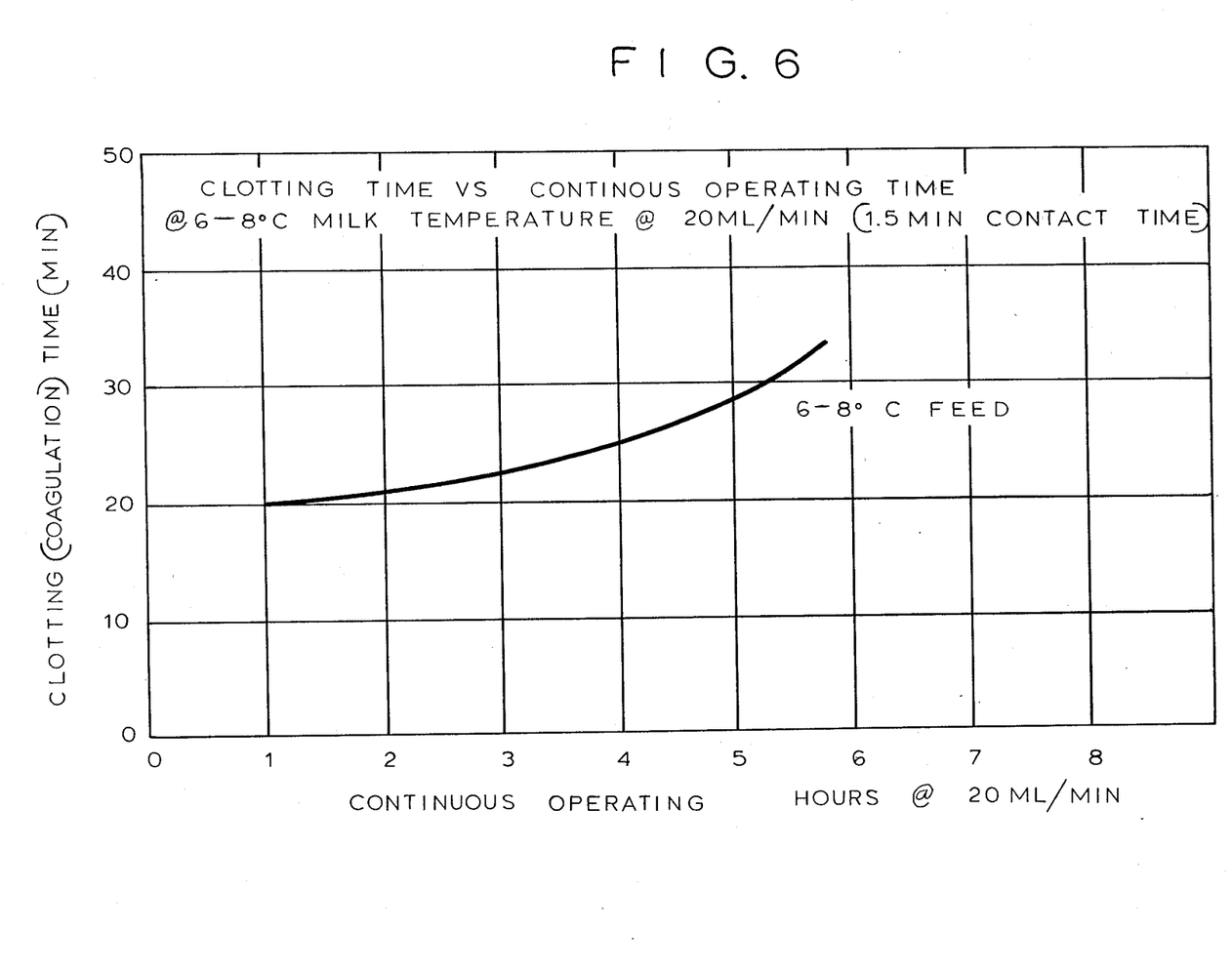
FIG. 6 illustrates long term clotting effects at a certain flow rate in a continuous operation.

After six hours of continuous operation as shown in FIG. 6 at low feed temperature (6° C.) and low flow rate (20 ml/min at 1.5 min. residence or contact time) a slight loss of activity was observed, possibly due to the deposition of protein on the surface. Higher feed-temperatures and higher flow rates help to minimize substantially entirely this problem. Both microbial and calf rennet were tried. Protease enzymes such as pepsin or alkaline protease are also useful.

For this example, a commercially obtainable calf rennet clotting enzyme was used. It contains approximately 95% chymosin and 5% pepsin.

A spiral reactor, 3" high×1" ID×2¼" OD, as described previously, was made and immobilized with rennet enzyme using the standard immobilization process mentioned above. Skim milk was used as the substrate.

A clotting test unit consists of a 30° C. water bath, a test vessel in which the treated substrate is held and which is rotated by an electric motor. Rotation is at about 4-10 RPM.

The continuous coagulation system was run as follows. A vessel for milk, a cooling coil, and the above described reactor were enclosed in a water bath which was then controlled at about 6°-8° C. and 14° C. and 19° C., or at any other preselected temperature. The reactor was first flushed with a pH 6.5 buffer (0.5 gm sodium acetate per liter), followed with skim milk at the desired temperature, with various flow rates to determine the effect of both temperature and residence time on the coagulation time being thereby observed. Skim milk was also pumped through the reactor at a constant flow rate for a period of 6-8 hours to see if any change on activity occurs.

The reactor was run each day for approximately six hours at one desired temperature. The reactor was then cleaned up with (a) 6.5 pH buffer (30 min) and followed with (b) 6.5 pH buffer containing 0.05% hydrogen peroxide (30 min) and stored in refrigerator for the next day trial.

Clotting time tests were established as follows. Ten milliliters of the treated skim milk effluent were collected from the reactor in the test vessel. The vessel was rotated at 4-10 RPM in 30° C. water to determine both initial (flake on wall) and completed clotting time (gel-like on the whole surface of the 10 ml). However, it was found that many factors, such as size of coagulum, effluent feed temperature, heat transfer rate, etc., affect the initial coagulation time results. The completed coagulation time for 10 ml sample was used for this study.

Figure 5:
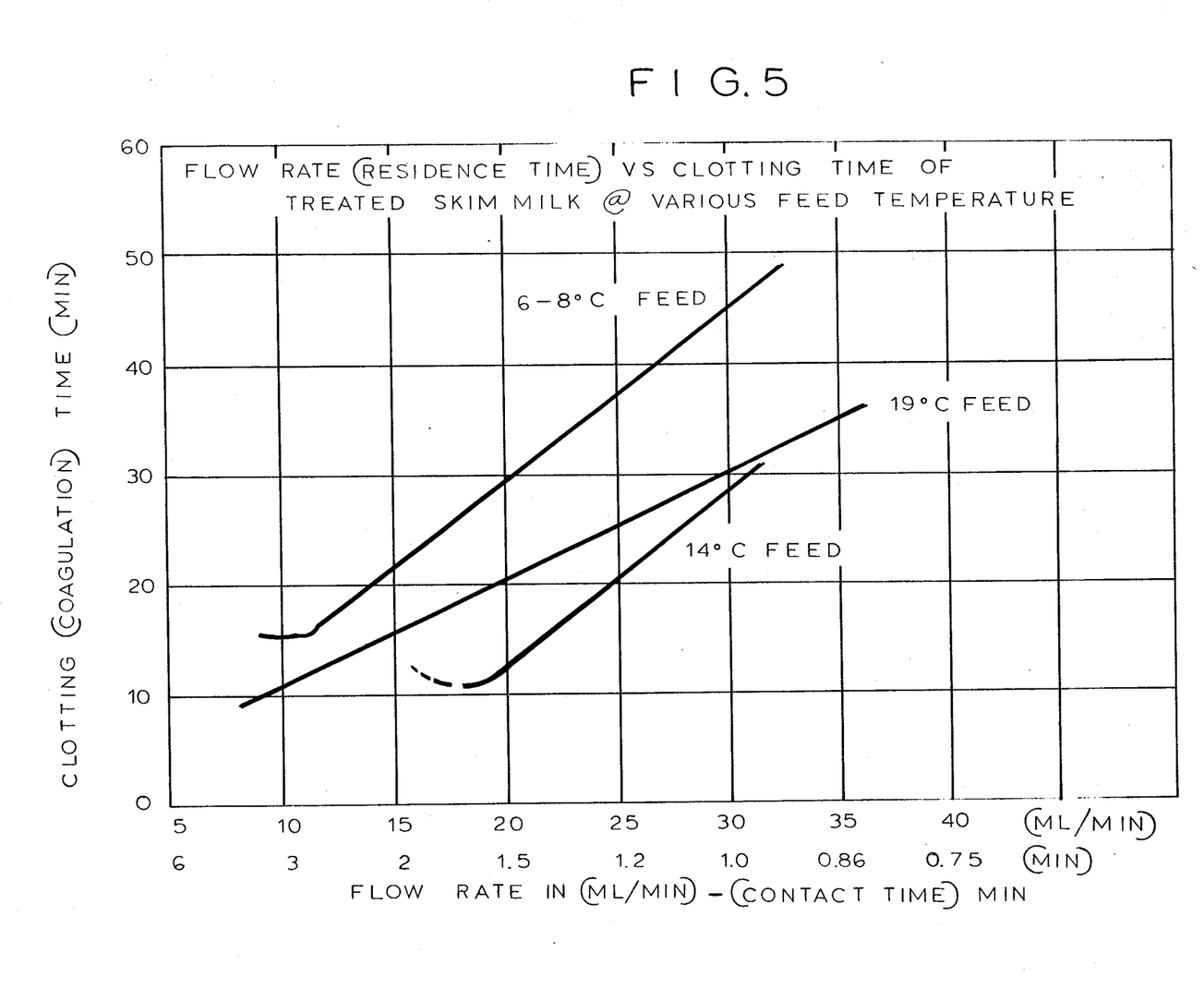
FIG. 5 illustrates the feed rate versus clotting (coagulation) time at various feed (substrate) temperatures.

FIG. 5 presented a series of clotting tests on the rennet reactor skim milk samples which were run with various flow rates at different temperatures. Activity is expressed as clotting time (min.) which is the time for a sample of skim milk (10 ml) to clot completely under 30° C. The results indicated that a continuous coagulation process is achieved. At 6°-8° C. milk feed temperature, it took 30 min. and 45 min. to clot the treated milk with a flow rate of 20 ml/min. (1.5 min. residence, i.e. constant time) and 30 ml/min. (1. min residence time) respectively. If the feed temperature was increased to 19° C., the clotting time was decreased from 30 min to 20 min and 45 min. to 30 min. with same above flow rates. Thus, the clotting time can be controlled by regulating both flow rate and feed temperature.

As shown in FIG. 6, skim milk (6°-8° C. temperature) was continuously pumped through the reactor with a constant flow rate of 20 ml/min. (1.5 min. residence time). The effluent was then collected at various operating hours for the clotting test. The results indicated that the clotting time increased from 20 min. at first hour to 30 min. after six hours of continuous operation. This may indicate that some protein contamination deposits on the surface of the reactor which causes a slight loss in activity.

EXAMPLE 2

Figure 7:
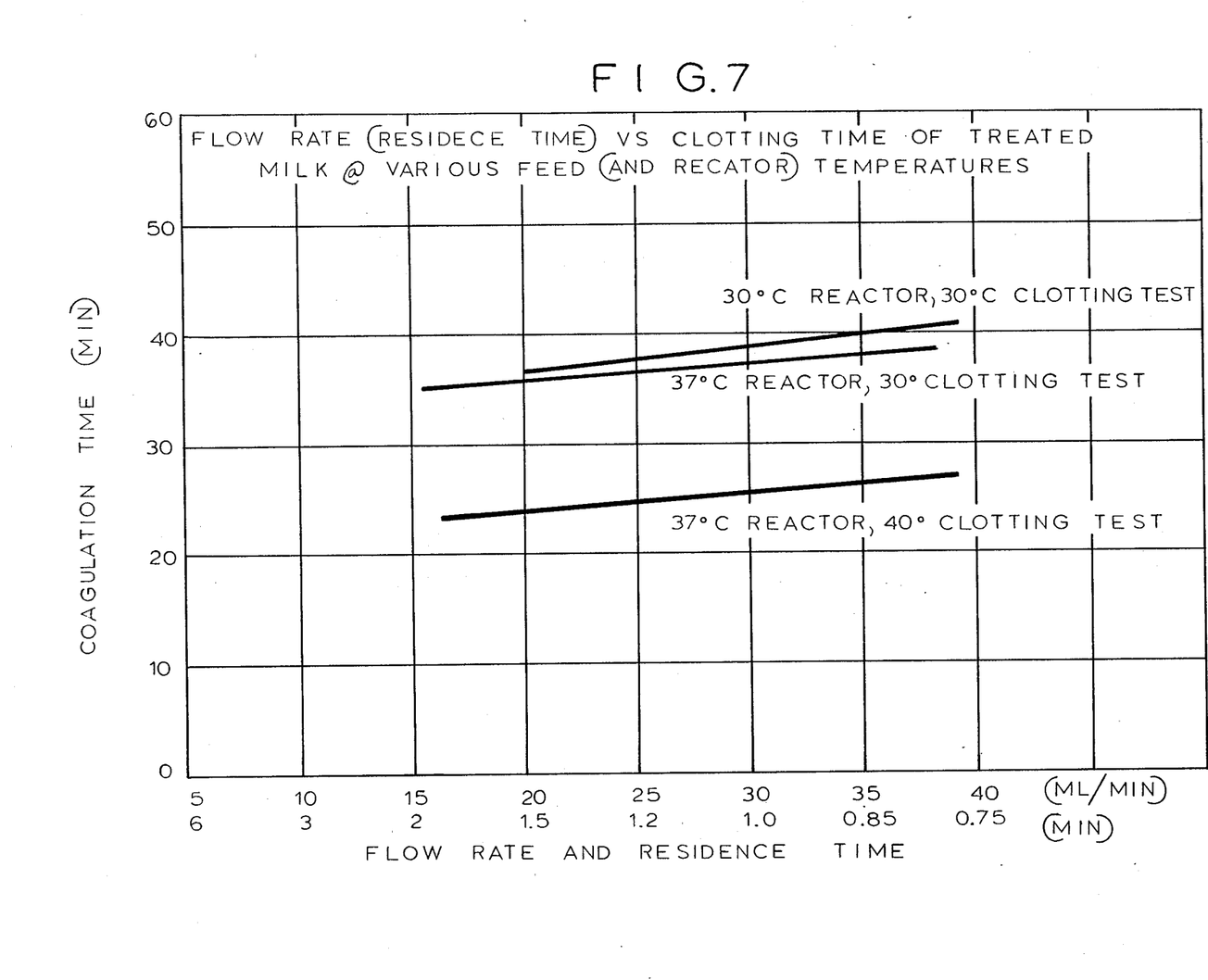
FIG. 7 illustrates coagulation time versus flow rate (or residence time) at elevated temperatures.

Typically in the manufacture of cheese milk, either skim or whole milk is first pasteurized and then cooled to 32° C. (about 88° F.). Thereafter a starter culture and rennet are added. In the present example and as shown in FIG. 7, the clotting (i.e. coagulation time) has been illustrated as a function of substrate temperature and clotting temperature in the apparatus as described in Example 1. However, the advantages of the high temperature operations, e.g. 30° C. and 37° C., are evident as less cooling (or conversely heating) is necessary.

The procedure was as follows:

The calf rennet milk clotting enzyme was immobilized in the spiral reactor described above (size 3" long×2¼ O.D.) and run at 30° C. and 37° C. reactor temperature using both store bought pasteurized skim and whole milk as feedstocks. Coagulation tests were done at 30° C. and 40° C. using a 10 milliliter coagulation test procedure described in Example 1. From the data shown in FIG. 7, the following apply.

At 30° C. and 37° C., with a residence time of 0.75 min. and 1.5 min., coagulation did not take place inside the rennet immobilized reactor. It did occur in the external clotting test tube at 30° C. The coagulation took place inside the reactor at 30° C. if the skim milk was passed through the reactor system twice. This proves that by adjusting the residence time (or reactor size), it is possible to control the desired coagulation time. However, part of the reaction may have been initiated in the heating coil before the reactor, the material was enzyme treated already on the first pass.

Further, the clotting test at 40° C. gives a much faster clotting rate (approximately 30%) than at 30° C. The whole milk gave approximately 20% longer clotting time as compared to skim milk.

Based on operating conditions, milk can be processed through the reactor at 30° and 37° C. Coagulation or clotting external to or internal to the reactor was observed. The immobilized calf-rennet enzyme used in the reactor was approximately six months old.

FIG. 7 thus presents a series of test results at various reactor and feed temperatures and the resulting clotting test results at different temperatures. As mentioned before, skim milk and whole milk were first heated to 30° C. and 37° C. and passed through the reactor at the same respective temperatures. No coagulation and pressure drop increase in the reactor was observed. If the first pass treated milk is stored overnight in the refrigerator and then reheated and repassed through the reactor, the cogulation took place inside the housing and reactor, which indicates that the residence time is still a major factor affecting the clotting rate.

A reactor system that fits into a commercial process for continuous coagulation of 30° C. or 37° C. is practical. As shown in FIG. 7, the clotting test at 40° C. gave a much faster clot rate than at 30° C. For example, with a reactor residence time of 1 minute, it takes 26 minutes clot time at 40° C. as compared to 38 minutes at 30° C. Whole milk gave slightly longer clot time as compared to skim milk.

Further, it was concluded that at 30° and 37° C. reactor temperatures, breakdown of casein occurs. Not to clot or coagulate in the reactor but external to it is practical. By adjusting the residence time, one may cause clotting or coagulation to occur in the immobilized enzyme reactor.

As the reactor can tolerate particulates, it is evident that not only cheese can be obtained by casein coagulation, but protein coagulation in the whey may also be practiced. Appropriate whey protein enzymes are available for immobilization from commercial sources.

Still further, immobilization of rennet allows its use even after prolonged storage (under appropriate conditions). The treated substrate is rennet free and rennet thereafter does not continue to cause further reactions in the product. Precise control, e.g. residence time, flow rate, temperature, are possible. As milk is free from rennet up to the time it flows through the reactor, the unreacted milk flow may be stopped and diverted, thus allowing swing capacity for different cheeses and also for storage of unreacted milk. Moreover, starter culture may be added shortly before the milk is introduced in the reactors. Hence not only rennet under or over addition is avoided, but also starter contact and addition is easily and precisely controlled. Various renneting contact times at various temperatures at various coagulation temperatures introduce also great flexibility in cheese making processes.

What is claimed is:

1. A continuous process for making cheese comprising:
    continuously flowing a substrate containing coagulatable constituents through a spiral flow path defined by a spirally wound sheet, said sheet containing within it an immobilized enzyme that causes the substrate to coagulate;
    coagulating the substrate and converting the resultant coagulate into cheese;
    said flow path being between adjacent surfaces of said spirally wound sheet containing said immobilized enzyme, said sheet being microporous and having micro-pores that interconnect adjacent flow paths formed by said spirally wound sheet, said adjacent surfaces being spaced apart by a spacer that is spirally wound with said microporous sheet, and said spacer being selected from a group consisting of: (a) a plurality of microporous ribs on said spirally wound sheet disposed longitudinally to said flow path, and (b) a further sheet having an open net form.

2. The process as described in claim 1 wherein said spacer consists of said microporous ribs and also contains said immobilized enzyme.

3. The process as defined in claim 1 wherein said substrate is reacted in said flow path at a temperature at least 5° C.

4. The process as defined in claim 1 wherein the substrate is reacted in a first flow path as defined in claim 1 at one temperature, and thereafter reacted again in a second flow path as defined in claim 1 at a different temperature.

5. The process as defined in claim 1 wherein precise, predetermined temperature and contact time between said substrate and enzyme are maintained.

6. The process as defined in claim 1 wherein precise ratios of substrate to enzyme as based on contact time are maintained, thereby maintaining precise quality control.

7. The process as defined in claim 1 wherein said enzyme is rennet.

8. The process as defined in claim 1 wherein said enzyme is rennet and said substrate is milk.

9. The process as defined in claim 1 wherein said rennet is calf rennet.

10. The process as defined in claim 1 wherein the substrate is milk and it is treated at a temperature of up to 40° F.

11. The process as defined in claim 1 wherein the pH of the substrate to be treated is at a value from 5 to 6.7.

12. The process as defined in claim 1 wherein partial reaction takes place in said flow path and completion of said reaction and coagulation is in a reactor therefor.

13. The process as defined in claim 1 wherein said spacer is said sheet having open net form.

14. The process as defined in claim 1 wherein the spirally wound microporous sheet is made from a polyethylene silica composition.

15. The process as defined in claim 1 wherein the spirally wound microporous sheet is made from a polyvinyl chloride-silica composition and said immobilized enzyme is immobilized on said silica.

16. The process as defined in claim 1 wherein the spirally wound microporous sheet is formed from a sulfur-free cured natural rubber.

17. The process as defined in claim 1 wherein an enzyme reaction takes place at a residence time from about 0.5 to 5 minutes.

18. The process as defined in claim 1 wherein an enzyme reaction in said substrate is for a period of 0.5 to 10 minutes.

19. The process as defined in claim 1 wherein the spacing between adjacent surfaces is between 0.003 and 0.050 inches.

20. The process as defined in claim 1 wherein prior to introduction of said substrate in said flow path, said substrate is inoculated with a bacterial culture to achieve a desired acidity.

* * * * *

UNITED STATES PATENT AND TRADEMARK OFFICE
CERTIFICATE OF CORRECTION

PATENT NO. : 4,801,463

DATED : January 31, 1989

INVENTOR(S) : Bruce S. Goldberg et al.

It is certified that error appears in the above-identified patent and that said Letters Patent is hereby corrected as shown below:

Column 9, line 12, "constant" should read -- contact --.

Signed and Sealed this

Fourth Day of July, 1989

Attest:

DONALD J. QUIGG

Attesting Officer

Commissioner of Patents and Trademarks